United States Patent
Matsuura

(10) Patent No.: US 8,229,067 B2
(45) Date of Patent: Jul. 24, 2012

(54) RADIATION IMAGING APPARATUS AND DARK CURRENT CORRECTION METHOD THEREFOR

(75) Inventor: Tomohiko Matsuura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 214 days.

(21) Appl. No.: 12/723,814

(22) Filed: Mar. 15, 2010

(65) Prior Publication Data

US 2010/0245378 A1      Sep. 30, 2010

(30) Foreign Application Priority Data

Mar. 31, 2009   (JP) ................................. 2009-087837

(51) Int. Cl.
G09G 5/02      (2006.01)
G01N 23/04     (2006.01)
G06K 9/00      (2006.01)

(52) U.S. Cl. ........................... 378/62; 382/132; 345/589

(58) Field of Classification Search .................... 378/62, 378/98.8, 42, 91, 98.12, 207; 345/589; 382/132
See application file for complete search history.

(56) References Cited

U.S. PATENT DOCUMENTS

| | | | | |
|---|---|---|---|---|
| 7,810,997 B2 * | 10/2010 | Okamura | | 378/207 |
| 7,819,581 B2 * | 10/2010 | Srinivasan et al. | | 378/207 |
| 2003/0223539 A1 * | 12/2003 | Granfors et al. | | 378/98.8 |
| 2006/0188061 A1 * | 8/2006 | Takenaka et al. | | 378/62 |
| 2007/0125952 A1 | 6/2007 | Endo et al. | | 250/369 |
| 2008/0246065 A1 | 10/2008 | Takenaka et al. | | 257/292 |

FOREIGN PATENT DOCUMENTS

| | | |
|---|---|---|
| CN | 101282427 | 10/2008 |
| EP | 1978730 | 10/2008 |
| JP | H07-236093 | 9/1995 |
| JP | 2007-082729 | 4/2007 |
| JP | 2007-222501 | 9/2007 |

OTHER PUBLICATIONS

Chinese Office Action dated Jul. 7, 2011, issued in counterpart Chinese Patent Application No. 201010141919.4, and English translation.

* cited by examiner

*Primary Examiner* — Irakli Kiknadze
(74) *Attorney, Agent, or Firm* — Fitzpatrick, Cella, Harper & Scinto

(57) ABSTRACT

A radiation imaging apparatus comprises a radiation detection unit that detects radiation, an instruction unit that issues a radiation-imaging start instruction, and a setting unit to set an irradiation delay period that extends between the issuance of an imaging start instruction and the time irradiation begins. A first acquisition unit acquires a plurality of dark current images during the set irradiation delay period, and a second acquires a radiation image of the object after the end of the set irradiation delay period. A correction data generation unit generate correction data for the acquired radiation image, based on the dark current images, and a correction unit executes dark current correction processing of the acquired radiation image using the correction data.

15 Claims, 6 Drawing Sheets

FIG. 7

| IMAGING REGION | IRRADIATION DELAY TIME [sec] |
|---|---|
| CHEST REGION | 0.3 |
| ABDOMINAL REGION | 0.5 |
| EXTREMITIES | 0.6 |
| CHILD'S CHEST REGION | 0.1 |
| HEAD REGION | 0.6 |
| | |

RADIATION IMAGING APPARATUS AND DARK CURRENT CORRECTION METHOD THEREFOR

BACKGROUND OF THE INVENTION

1. Field of the Invention

The present invention relates to a radiation imaging apparatus that obtains radiation images and a dark current correction method for the apparatus.

2. Description of the Related Art

In obtaining radiation images (for example, X-ray images), an X-ray image of an object is acquired by using a film/screen with a cassette holding a film and an intensifying screen or an image plate in a cassette which is used for computed radiography.

Recently, X-ray detectors that directly convert X-ray images into digital signals in real time have been proposed. Such X-ray detectors include, for example, an X-ray detector having a solid-state photodetector and a scintillator stacked on each other. The solid-state photodetector has solid-state photodetection elements, each formed from a transparent conductive film and a conductive film, arrayed in a matrix form on an amorphous semiconductor on a substrate made of silica glass. The scintillator converts X-rays into visible light.

There are also various known X-ray detectors that directly acquire X-rays with solid-state photodetectors without using a scintillator. Such an X-ray detector is free from the influence of light scattering caused by a scintillator unlike an X-ray detector using a scintillator, and hence is generally considered to have a high resolution. An X-ray detector that includes a combination of a CCD or CMOS detector and a scintillator to increase the number of images taken per unit time, is also known.

In general, these X-ray detectors detect the intensities of X-rays as electric charge quantities. For this reason, in order to acquire an X-ray image, it is necessary to reset the electric charges in pixels, accumulate electric charges, transfer the electric charges in pixels, and perform driving in a predetermined cycle.

In an X-ray detector, the electric charges of dark current components proportional to the accumulation time of signal charges generated by X-rays are accumulated together with the signal charges. For this reason, an acquired X-ray image contains X-ray signal components and dark current components, and hence dark current correction processing is performed in X-ray imaging. In dark current correction processing, a dark current image containing only dark current components is acquired without X-ray irradiation. The acquired dark current image is then subtracted from the X-ray image to remove the dark current components from the X-ray image.

In this case, as described above, a dark current image is acquired without X-ray irradiation. For this reason, in general, when obtaining a still image, the X-ray detector acquires the image immediately before or after X-ray irradiation. When obtaining a moving image typified by an X-ray fluoroscopic image, since it is generally necessary to observe an X-ray image in real time, the X-ray detector acquires the image before or between times of X-ray irradiation. In high-speed imaging such as IVR, angiography, or CT, in which a larger number of images (for example, 60 fps) are acquired per unit time, it is difficult to acquire a dark current image between times of X-ray irradiation. For this reason, in such a case, the X-ray detector often uses a dark current image acquired before X-ray irradiation.

In general, however, in such an X-ray detector, dark current components are often unstable immediately after driving has started. In order to improve the quality of an obtained image, therefore, it is necessary to secure a certain period of time from the start of driving to X-ray irradiation. On the other hand, in order to improve the operability of an X-ray imaging apparatus, it is preferable to quickly start X-ray irradiation when the operator presses the start switch (for example, the X-ray irradiation switch).

To eliminate this tradeoff, Japanese Patent Laid-Open No. 07-236093 discloses a technique of changing and using dark current components stored in advance, in accordance with an imaging time, the temperature of a solid-stage imaging device, a pixel value, a pixel position, and the like. Japanese Patent Laid-Open No. 2007-222501 also discloses a technique of dividing the time between the driving starting (power being applied) and the pixel characteristics becoming stable into a plurality of intervals and measuring and storing dark current components in the respective intervals in advance. This technique performs correction by subtracting a dark current component corresponding to each interval at the time of imaging.

As in the case of the technique disclosed in Japanese Patent Laid-Open No. 07-236093, when dark current components stored in advance are to be changed and used in accordance with the situation at the time of imaging, it is necessary to monitor the situation at the time of imaging. This makes it necessary to provide a new arrangement. In addition, it is difficult to accurately change dark current components in accordance with all the situations that can occur.

As in the case of the technique disclosed in Japanese Patent Laid-Open No. 2007-222501, when dark current components after the start of driving are to be stored in the respective intervals, it is impossible to give sufficient consideration to errors due to actual situations at the time of imaging, for example, the imaging frame rate and the temperature of the solid-state imaging device.

A simple measure to eliminate the above tradeoff is to stabilize dark current components by always driving an X-ray detector, i.e., always energizing it. In this case, however, there is a fear that, for example, the power consumption will increase and the service life of the apparatus will shorten.

SUMMARY OF THE INVENTION

The present invention provides a technique of executing dark current correction processing by using correction data generated based on a plurality of dark current images detected in the interval between an imaging start instruction being issued and the X-ray irradiation starting.

According to a first aspect of the present invention, there is provided a radiation imaging apparatus, for obtaining a radiation image of an object, the apparatus comprising: an irradiation unit; a radiation detection unit configured to detect radiation; an instruction unit configured to issue a radiation imaging start instruction; a setting unit configured to set an irradiation delay period between the time the instruction unit issues an imaging start instruction and the time irradiation by the irradiation unit starts; a first acquisition unit configured to acquire a plurality of dark current images, from the radiation detection unit, during the irradiation delay period set by the setting unit; a second acquisition unit configured to acquire a radiation image of the object from the radiation detection unit after the end of the irradiation delay period set by the setting unit; a correction data generation unit configured to generate correction data, for the radiation image acquired by the second acquisition unit, based on the plurality of dark current images acquired by the first acquisition unit; and a correction unit configured to execute dark current correction processing of the radiation image acquired by the second acquisition unit, by using the correction data generated by the correction data generation unit.

According to a second aspect of the present invention, there is provided a dark current correction method for a radiation imaging apparatus, the radiation imaging apparatus including an irradiation unit and a radiation detection unit, the method comprising the steps of: issuing a radiation imaging start instruction; setting an irradiation delay period between the time the imaging start instruction is issued and the time irradiation by the irradiation unit starts; acquiring a plurality of dark current images from the radiation detection unit during the set irradiation delay period; acquiring a radiation image, of an object, based on radiation detected by the radiation detection unit after the end of the set irradiation delay period; generating correction data for the acquired radiation image of the object, based on the acquired plurality of dark current images; and executing dark current correction processing on the radiation image of the object using the generated correction data.

Further features of the present invention will be apparent from the following description of exemplary embodiments with reference to the attached drawings.

BRIEF DESCRIPTION OF THE DRAWINGS

FIG. 7 is a view showing an example of the correspondence relationship between imaging regions and irradiation delay times.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

Although the following embodiments will exemplify cases in which X-rays are used as radiation, radiation is not limited to X-rays, and it is possible to use electromagnetic waves including γ-rays and also particulate beams such as α-rays, β-rays and the like, within the scope of the invention.

First Embodiment

Figure 1:
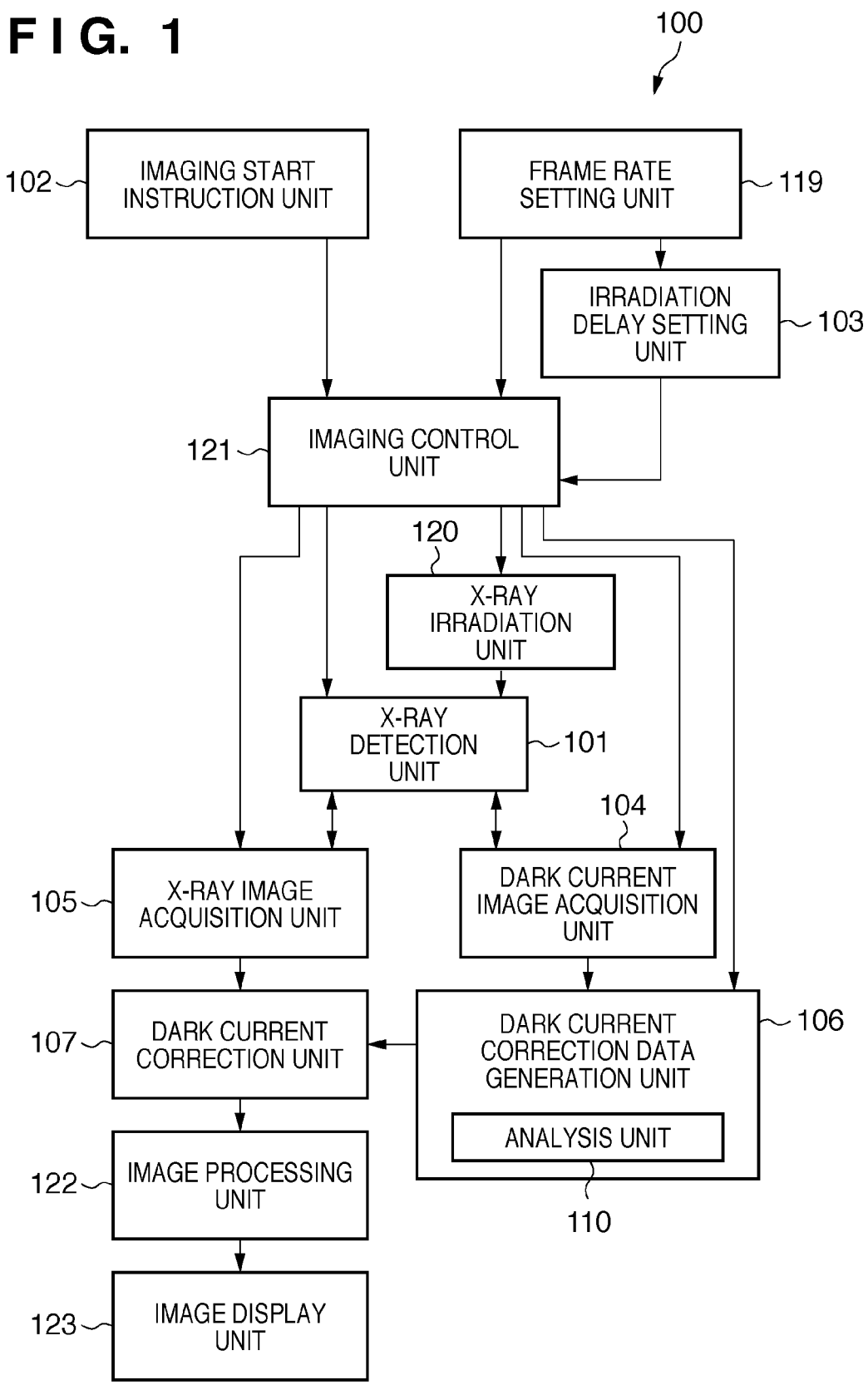
FIG. 1 is a block diagram showing the arrangement of an X-ray imaging apparatus 100 according to an embodiment of the present invention.

FIG. 1 is a block diagram showing an example of the arrangement of an X-ray imaging apparatus 100 according to an embodiment of the present invention.

The X-ray imaging apparatus 100 includes one or a plurality of computers. A computer includes, for example, a main control unit such as a CPU and storage units such as a ROM (Read Only Memory) and a RAM (Random Access Memory). The computer may also include a communication unit such as a network card and input/output units such as a keyboard, a mouse, a display, and a touch panel. Note that these constituent elements are connected to each other via a bus and the like and are controlled by causing the main control unit to execute programs stored in a storage unit.

In this case, the X-ray imaging apparatus 100 includes an X-ray detection unit 101, an imaging start instruction unit 102, an irradiation delay setting unit 103, a dark current image acquisition unit 104, an X-ray image acquisition unit 105, a dark current correction data generation unit 106, and a dark current correction unit 107. The X-ray imaging apparatus 100 is also provided with a frame rate setting unit 119, an X-ray irradiation unit 120, an imaging control unit 121, an image processing unit 122, and an image display unit 123.

The X-ray irradiation unit 120 functions as a radiation irradiation unit and irradiates (emits) radiation (X-rays) to an object (for example, a human body). The frame rate setting unit 119 sets a frame rate at the time of X-ray imaging.

The X-ray detection unit 101 functions as a radiation detection unit and detects the radiation transmitted through an object. This allows the X-ray imaging apparatus 100 to obtain a radiation image (an X-ray image in this embodiment) based on the object. The imaging start instruction unit 102 issues an X-ray imaging start instruction. The imaging start instruction unit 102 issues an imaging start instruction based on, for example, operation by the operator (e.g. pressing an X-ray emission switch).

The irradiation delay setting unit 103 sets the time (to be referred to as an irradiation delay time hereinafter) from the time at which the imaging start instruction unit 102 issues an imaging start instruction to the time X-ray irradiation starts so in other words the period between the issuance of the imaging start instruction and the start of X-ray irradiation. The dark current image acquisition unit 104 reads out and acquires a plurality of dark current images from the X-ray detection unit 101 until the irradiation delay time set by the irradiation delay setting unit 103 elapses after the imaging start instruction unit 102 issues an imaging start instruction.

The X-ray image acquisition unit 105 functions as a radiation image acquisition unit and reads out and acquires one or a plurality of X-ray images based on the X-rays detected by the X-ray detection unit 101. The X-ray image acquisition unit 105 repeatedly acquires X-ray images while the X-ray irradiation unit 120 is irradiating X-rays after the lapse of the irradiation delay time.

The dark current correction data generation unit 106 generates dark current correction data based on a plurality of dark current images acquired by the dark current image acquisition unit 104. The dark current correction data generation unit 106 generates dark current correction data in accordance with one or a plurality of X-ray images acquired by the X-ray image acquisition unit 105. The dark current correction data generation unit 106 is provided with an analysis unit 110 that analyzes a plurality of dark current images. That is, the dark current correction data generation unit 106 generates dark current correction data based on the analysis result obtained by the analysis unit 110.

The dark current correction unit 107 removes dark current components from the one or plurality of X-ray images acquired by the X-ray image acquisition unit 105 by executing dark current correction processing for the X-ray images. The dark current correction unit 107 performs dark current correction processing by subtracting the dark current correction data generated by the dark current correction data generation unit 106 from the X-ray images acquired by the X-ray image acquisition unit 105.

The image processing unit 122 executes image processing for the X-ray images after the dark current correction. Note that the image processing includes, for example, emphasis processing, dynamic range compression processing, a noise reduction process, and halftone processing. The image display unit 123 displays the X-ray images processed by the image processing unit 122.

The imaging control unit 121 comprehensively controls imaging processing in the X-ray imaging apparatus 100. Although not shown in FIG. 1, the imaging control unit 121 is connected to the respective components. The imaging control unit 121 controls, for example, processing such as driving of the X-ray detection unit 101 and X-ray irradiation by the X-ray irradiation unit 120.

Although an example of the arrangement of the X-ray imaging apparatus 100 has been described so far, the components provided in the apparatus need not be implemented in the manner shown in shown in FIG. 1. For example, the respective functional arrangements described above may be arranged in a plurality of devices and implemented as a system.

Figure 2:
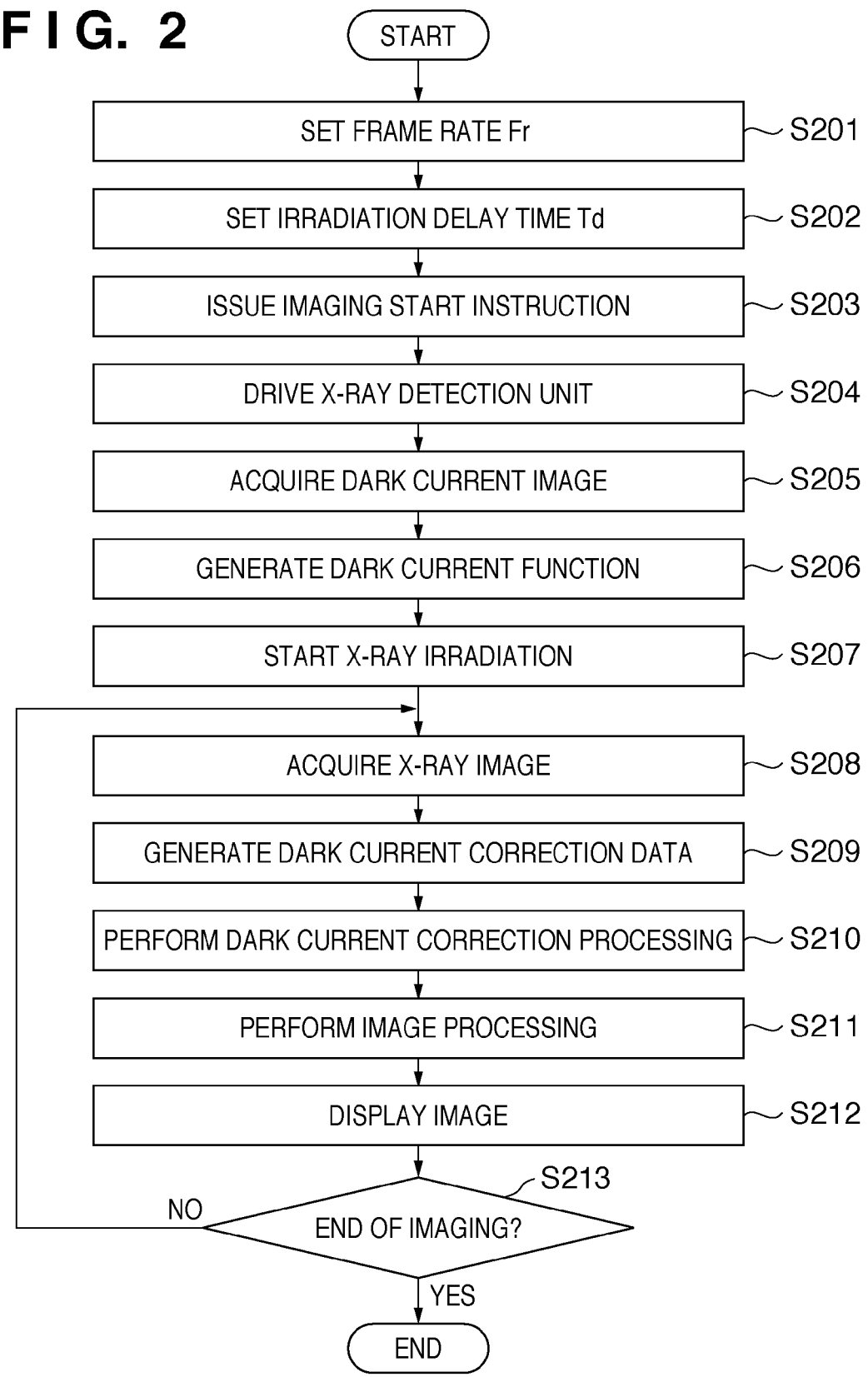
FIG. 2 is a flowchart showing an example of a procedure for processing in the X-ray imaging apparatus 100 shown in FIG. 1.
Figure 3:
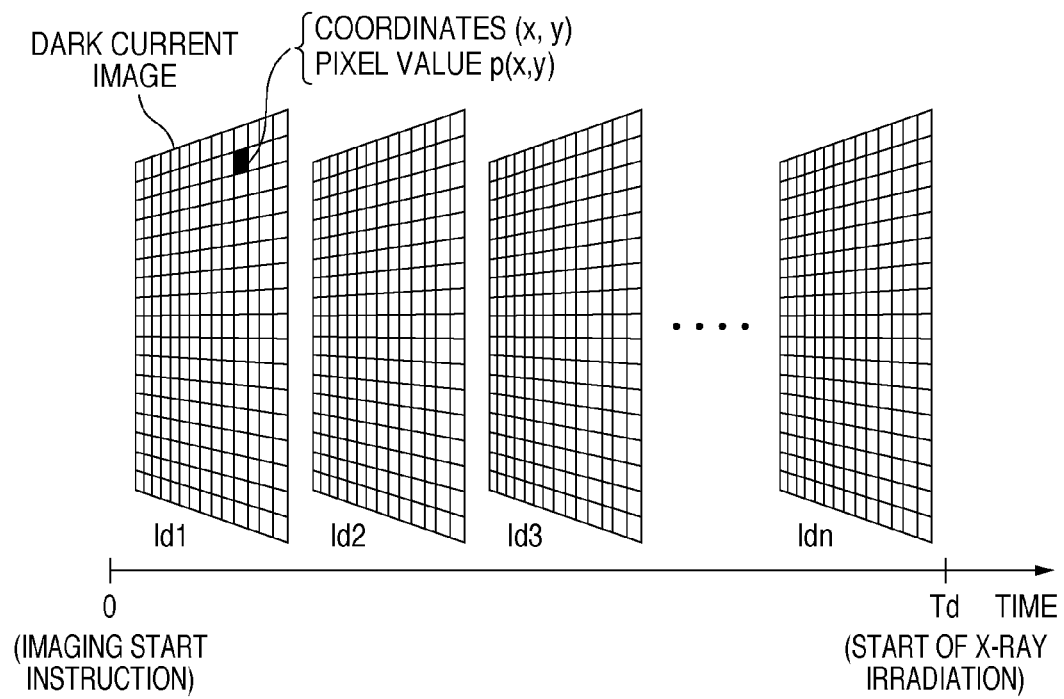
FIG. 3 is a view showing an example of an overview of dark current images.
Figure 4:
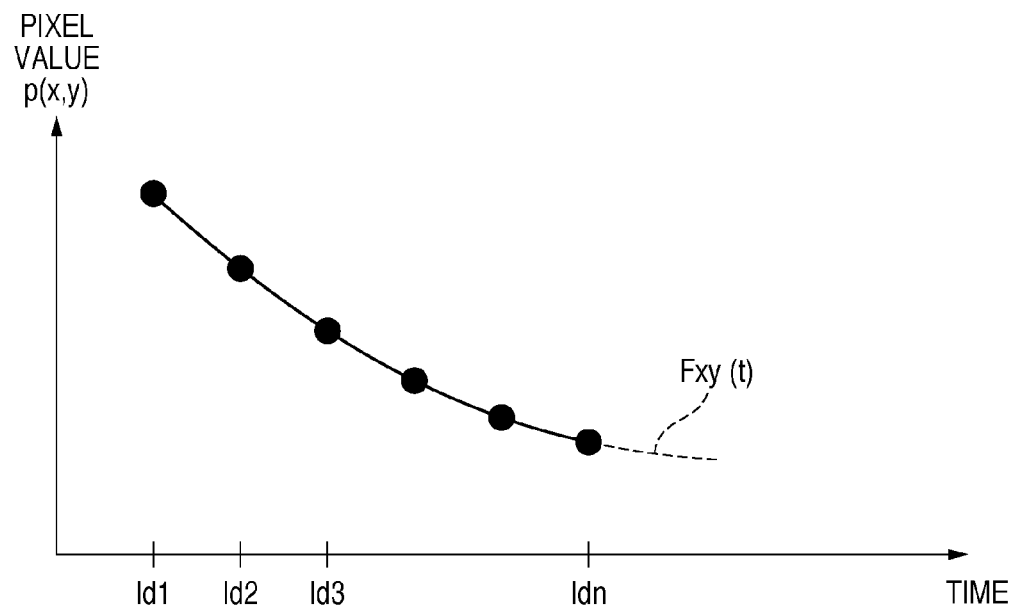
FIG. 4 is a graph showing an example of an overview of how the pixel value of a given pixel in a dark current image changes.

An example of imaging processing in the X-ray imaging apparatus 100 shown in FIG. 1 will be described next with reference to FIGS. 2 to 4. FIG. 2 is a flowchart showing an example of a procedure for processing in the X-ray imaging apparatus 100 shown in FIG. 1. FIG. 3 is a view showing an example of an overview of dark current images. FIG. 4 is a graph showing an example of an overview of how the pixel value of a given pixel in a dark current image changes.

When this processing starts, first of all, the X-ray imaging apparatus 100 causes the frame rate setting unit 119 to set a frame rate Fr at the time of X-ray imaging (S201). The set value of the frame rate Fr is automatically set in accordance with an imaging technique. In this case, for example, the frame rate Fr is set to 60 [fps].

Upon setting a frame rate, the X-ray imaging apparatus 100 causes the irradiation delay setting unit 103 to set an irradiation delay time Td indicating the time from the time an imaging start instruction is issued to the time X-ray irradiation starts (S202). If a long irradiation delay time is set in this case, since dark current images can be acquired in a state in which dark current components are stable, the quality of images obtained by imaging improves. If a short irradiation delay time is set, since the apparatus quickly performs X-ray irradiation, the operability improves. Although the set value of an irradiation delay time and the setting method are not specifically limited, it is assumed that the apparatus automatically sets a predetermined fixed value (Td=0.3 [sec]) in this embodiment.

The X-ray imaging apparatus 100 causes the imaging start instruction unit 102 to issue an X-ray imaging start instruction (S203). As described above, the imaging start instruction unit 102 issues this instruction based on operation by the operator (e.g. pressing the X-ray emission switch).

Upon issuing an imaging start instruction, the X-ray imaging apparatus 100 causes the imaging control unit 121 to drive the X-ray detection unit 101 (S204). The X-ray imaging apparatus 100 causes the dark current image acquisition unit 104 to acquire a plurality of dark current images detected by the X-ray detection unit 101 until the irradiation delay time Td elapses after the imaging start instruction is issued in the processing in step S203 (S205). FIG. 3 schematically shows dark current image acquisition processing in step S205. The abscissa represents the elapsed time from the issuance of an imaging start instruction. Reference symbols Id1, Id2, Id3, . . . , Idn denote dark current images acquired at the frame rate Fr. A dark current image holds a pixel value p(x, y) for each pixel, where each pixel is specified or denoted by coordinates (x, y).

The X-ray imaging apparatus 100 then causes the analysis unit 110 to generate a dark current function Fxy(t) representing a change over time in each pixel value using the plurality of dark current images (S206). In other words a function Fxy(t), representing the change in pixel value over time, is generated for each pixel using the plurality of dark current images. More specifically, as shown in FIG. 4, assuming that the pixel value p(x, y) for each pixel denoted by the coordinates (x, y) in each of the dark current images Id1, Id2, Id3, . . . , Idn is known data, the dark current function Fxy(t) representing a change in pixel value in the time direction is generated. The dark current function Fxy(t) is generated for all the coordinates (x, y) in each dark current image. In other words a dark current function Fxy(t) is generated for each pixel in each dark current image.

There are various known methods of generating an approximate function (the dark current function Fxy(t) in this case) from a plurality of known data. The method to be used is not specifically limited. This embodiment generates an approximate function which is characterized by being either monotone non-increasing (also known as monotonically non-increasing) or monotone non-decreasing (also known as monotonically non-decreasing) with respect to an increase in elapsed time, which is one of the typical characteristics of a dark current component, and by converging to a predetermined value at infinity of the elapsed time. For example, the embodiment estimates A, B, and C from an exponential function model "Fxy(t)=A·exp(B·t)+C" (where t represents the elapsed time after the issuance of an imaging start instruction). With this operation, the embodiment generates an approximate function. In this case, C represents a convergence value at infinity of the elapsed time. It is known that if C is a known value, A and B can be estimated by the least squares method, and it is possible to calculate an R-squared value as one of the adequate indexes for the approximate function. For this reason, a given initial value is assigned to C, and a search is made for A and B which maximize the R-squared value while changing C. This makes it possible to generate the dark current function Fxy(t). It is also possible to perform the above estimation by using a plurality of function models and select one of the function models, set as approximate function candidates, based on adequate index.

Upon generating the dark current functions for each of the pixels, the X-ray imaging apparatus 100 causes the X-ray irradiation unit 120 to start X-ray irradiation (S207). The X-ray irradiation unit 120 performs this irradiation under the control of the imaging control unit 121. The irradiated x-rays are transmitted through the object (not shown) while being attenuated, and reach the X-ray detection unit 101. As a consequence, electric charges representing a radiograph of the object are accumulated in the X-ray detection unit 101.

When starting X-ray irradiation, the X-ray imaging apparatus 100 repeats the processing from steps S208 to S212 to perform X-ray imaging processing. The X-ray imaging apparatus 100 executes this processing at a frequency corresponding to the frame rate Fr set in the processing in step S202. When starting the X-ray imaging processing, first of all, the X-ray imaging apparatus 100 causes the X-ray image acquisition unit 105 to acquire a radiograph of the object which is accumulated in the X-ray detection unit 101 as an X-ray image (S208). The X-ray imaging apparatus 100 causes the dark current correction data generation unit 106 to generate dark current correction data based on the dark current function Fxy(t) generated by the processing in step S207 and an elapsed time t from the issuance of an imaging start instruction (S209). More specifically, the dark current correction data generation unit 106 inputs the elapsed time t to the dark current function Fxy(t) generated in correspondence with each pixel at the coordinates (x, y) of the dark current image, and obtains an output value from the function for each pixel. The dark current correction data generation unit 106 visualizes (or obtains) the output value as the pixel value of the corresponding pixel, thereby generating dark current correction data.

Upon generating the dark current correction data, the X-ray imaging apparatus 100 causes the dark current correction unit 107 to obtain a correction image by executing dark current correction processing (S210). That is, the dark current correction unit 107 subtracts the relevant dark current correction data, as previously generated in correspondence with each X-ray image, from the corresponding one of the X-ray images acquired by the processing in step S208. In this case, to perform subtraction is to perform computation between the pixel values of pixels at corresponding coordinates between images. In other words the dark current data of each pixel is subtracted from the respective pixel value of the X-ray image.

After the image processing unit 122 executes image processing for each X-ray image after correction (S211), the X-ray imaging apparatus 100 causes the image display unit 123 to display the X-ray image having undergone the image processing (S212).

Subsequently, the X-ray imaging apparatus 100 determines whether an imaging end instruction is issued. For example, an imaging end instruction is issued based on operation by the operator (releasing the X-ray emission switch). If an imaging end instruction has been issued (YES in step S213), the processing is terminated; otherwise (NO in step S213), the process returns to step S208.

Note that an imaging end instruction need not always be based on operation by the operator. For example, an imaging end instruction may be automatically issued when a predetermined imaging time has elapsed.

As described above, the first embodiment generates correction data based on a plurality of dark current images detected in the interval between the time an imaging start instruction is issued and the time X-ray irradiation starts, and executes dark current correction processing by using the correction data. This makes it possible to execute accurate dark current correction in accordance with the situation at the time of imaging as compared with an apparatus which does not have this arrangement. For this reason, for example, the embodiment is free from the problem that the arrangement configured to correct dark currents by always driving an X-ray detection unit is subjected to an increase in power consumption and a decrease in the service life of the product. In addition, there is no need to provide any new arrangement for monitoring the situation, such as e.g. temperature of the imaging device, at the time of imaging.

Second Embodiment

Figure 5:
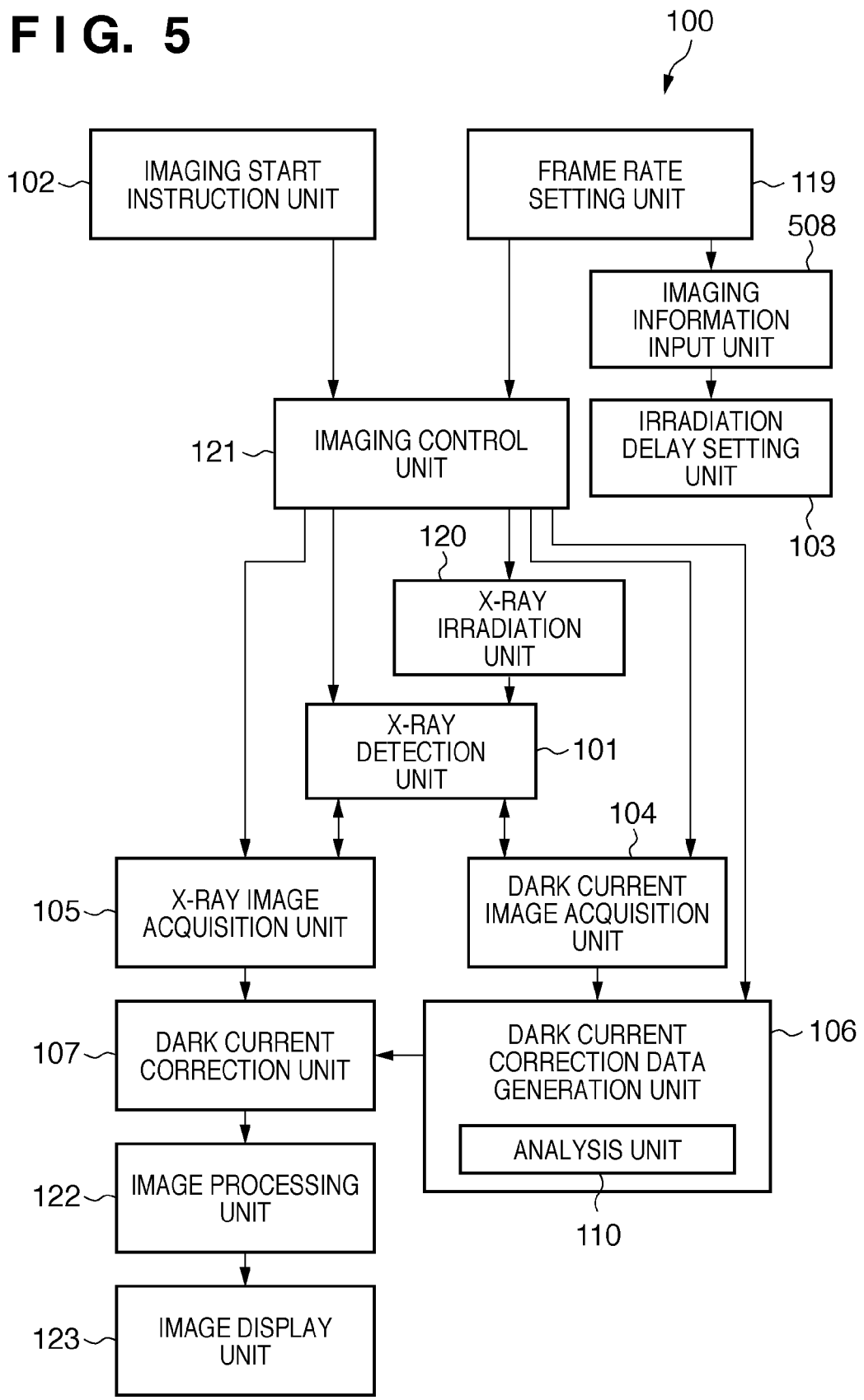
FIG. 5 is a block diagram showing an example of the arrangement of an X-ray imaging apparatus 100 according to the second embodiment.

The second embodiment will be described next. FIG. 5 is a block diagram showing an example of the arrangement of an X-ray imaging apparatus 100 according to the second embodiment. This arrangement differs from that shown in FIG. 1 described in the first embodiment in that it is provided with an imaging information input unit 508 which inputs imaging information concerning an object. Note that the remaining arrangement is the same as that in the first embodiment, and hence a description of the arrangement will be omitted, and the difference will be mainly described below.

Figure 6:
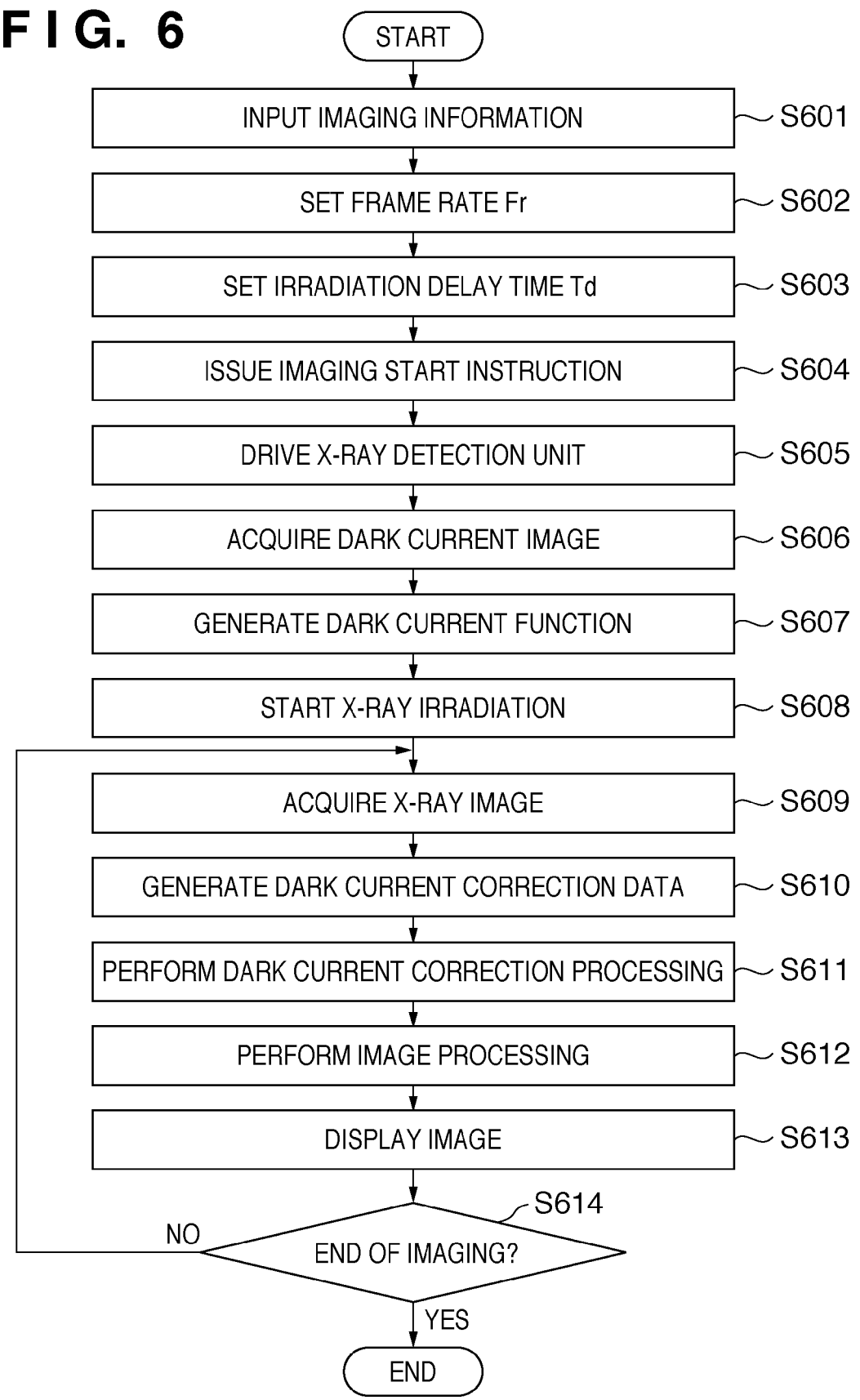
FIG. 6 is a flowchart showing an example of a procedure for processing in the X-ray imaging apparatus 100 according to the second embodiment.

An example of imaging processing in the X-ray imaging apparatus 100 according to the second embodiment will be described next with reference to FIGS. 6 and 7. FIG. 6 is a flowchart showing an example of a procedure for processing in the X-ray imaging apparatus 100 according to the second embodiment. FIG. 7 is a view showing an example of the correspondence relationship between imaging regions and irradiation delay times.

When starting this processing, first of all, the X-ray imaging apparatus 100 causes the imaging information input unit 508 to input imaging information from outside the apparatus (or inside the apparatus) and transmit the imaging information to an irradiation delay setting unit 103 (S601). The imaging information may be stored in advance in the information input unit, may be input to the input unit 508 from an internal storage means (e.g. memory) of the X-ray apparatus or may be input to the input unit 508 from an external storage means such as a CD, flash memory device, etc. The imaging information may also be input to the input unit 508 via a network such as a LAN, WAN or internet. The imaging information includes, for example, an imaging technique, an imaging region, an imaging body position, X-ray irradiation conditions (radiation irradiation conditions), an imaging request source, the size of an object (an object to be examined), and the age of the object. This embodiment will exemplify a case in which imaging information is an imaging region (for example, a chest region, an abdominal region, extremities, a child's chest region, and a head region). For example, imaging information is input based on operation by the operator via an operation panel or the like. Note that if imaging information is an imaging region, an imaging body position, or the like, the information may be automatically recognized on the apparatus side by pattern matching processing or the like.

The X-ray imaging apparatus 100 then causes a frame rate setting unit 119 to set a frame rate Fr at the time of X-ray imaging (S602). The set value of the frame rate Fr is automatically set in accordance with an imaging technique. In this case, the frame rate Fr is set to 60 [fps].

Upon setting the frame rate, the X-ray imaging apparatus 100 causes the irradiation delay setting unit 103 to set an irradiation delay time Td (S603). In this embodiment, an irradiation delay time is set based on the imaging information (the imaging region in this case) input by the processing in step S601. This optimally controls image quality and operability. An irradiation delay time based on an imaging region is set by using, for example, the table shown in FIG. 7 and the like. Assume that the table shown in FIG. 7 is to be used. In this case, if an imaging region is "child's chest region", Td=0.1 [sec], which is a relatively short period of time, is set. This is because, in imaging "child's chest region", importance is placed on the timing of the start of imaging. However, for e.g. the head region, less importance is placed on the timing of the start of imaging and Td=0.6[sec].

The X-ray imaging apparatus 100 then causes an imaging start instruction unit 102 to issue an X-ray imaging start instruction (S604). As described above, this instruction is issued based on, for example, operation by the operator (e.g. pressing the X-ray emission switch). Note that the processing in step S604 and the subsequent steps is the same as that in step S203 and the subsequent steps in FIG. 2 described in the first embodiment, and hence a description will not be repeated.

As described above, the second embodiment inputs imaging information and sets an imaging delay time based on the input imaging information. This makes it possible to perform imaging processing while satisfying both the requirements for the operability of the X-ray imaging apparatus and the quality of images obtained by imaging.

The above are examples of representative embodiments of the present invention. However, the present invention is not limited to the embodiments described above and shown in the accompanying drawings, and can be modified and embodied, as needed, within the scope in which the gist of the invention is not changed.

Note that the present invention can take embodiments as a system, apparatus, method, program, recording medium, and the like. More specifically, the present invention can be applied to a system including a plurality of devices, or to an apparatus embodied as a single device.

The present invention generates correction data based on a plurality of dark current images detected in the interval between the time an imaging start instruction is issued and the time radiation irradiation starts, and executes dark current correction processing by using the correction data. This makes it possible to accurately execute dark current correction in accordance with the situation at the time of imaging as compared with an apparatus which does not have this arrangement.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium). The program may be carried on a carrier medium such as a computer readable storage medium or transmission medium (signal).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-087837, filed Mar. 31, 2009 which is hereby incorporated by reference herein in its entirety.

What is claimed is:

1. A radiation imaging apparatus, for obtaining a radiation image of an object, the apparatus comprising:
    an irradiation unit;
    a radiation detection unit configured to detect radiation;
    an instruction unit configured to issue a radiation imaging start instruction;
    a setting unit configured to set an irradiation delay period between the time said instruction unit issues an imaging start instruction and the time irradiation by said irradiation unit starts;
    a first acquisition unit configured to acquire a plurality of dark current images, from said radiation detection unit, during the irradiation delay period set by said setting unit;
    a second acquisition unit configured to acquire a radiation image of the object from said radiation detection unit after the end of the irradiation delay period set by said setting unit;
    a correction data generation unit configured to generate correction data, for the radiation image acquired by said second acquisition unit, based on the plurality of dark current images acquired by said first acquisition unit; and
    a correction unit configured to execute dark current correction processing of the radiation image acquired by said second acquisition unit, by using the correction data generated by said correction data generation unit.

2. The apparatus according to claim 1, wherein said correction data generation unit comprises an analysis unit configured to analyze changes in the plurality of dark current images in a time direction, and generates the correction data corresponding to the radiation image based on an analysis result obtained by said analysis unit.

3. The apparatus according to claim 2, wherein
    said analysis unit generates a function representing changes in the plurality of dark current images in the time direction, and
    said correction data generation unit generates the correction data based on the function generated by said analysis unit and an elapsed time from the time said instruction unit issues the imaging start instruction to the time said second acquisition unit acquires the radiation image of the object.

4. The apparatus according to claim 3, wherein the function representing changes in the plurality of dark current images in the time direction is monotone non-increasing or monotone non-decreasing with respect to an increase in the elapsed time and by becoming constant at infinite time.

5. The apparatus according to claim 1, wherein said setting unit sets the irradiation delay period between said instruction unit issuing the imaging start instruction and the time the irradiation starts, based on imaging information of the object.

6. The apparatus according to claim 5, wherein the imaging information includes at least one of an imaging technique, an imaging region, an imaging body position, an X-ray irradiation condition, an imaging request source, a size of an object, and an age of the object.

7. The apparatus according to claim 1, further comprising:
    an image processing unit configured to execute image processing on the radiation image corrected by said correction unit; and
    a display unit configured to display the radiation image processed by said image processing unit.

8. A dark current correction method for a radiation imaging apparatus, said radiation imaging apparatus including an irradiation unit and a radiation detection unit, the method comprising the steps of:
    issuing a radiation imaging start instruction;
    setting an irradiation delay period between the time the imaging start instruction is issued and the time irradiation by the irradiation unit starts;
    acquiring a plurality of dark current images from the radiation detection unit during the set irradiation delay period;
    acquiring a radiation image, of an object, based on radiation detected by the radiation detection unit after the end of the set irradiation delay period;
    generating correction data for the acquired radiation image of the object, based on the acquired plurality of dark current images; and executing dark current correction processing on the radiation image of the object using the generated correction data.

9. A non-transitory computer-readable storage medium storing, in executable form, a program for causing a radiation imaging apparatus to implement the method of claim 8.

10. A radiation imaging comprising:
a radiation detection unit configured to detect radiation transmitted through an object;
an instruction unit configured to issue a radiation imaging start instruction;
a first acquisition unit configured to acquire a plurality of dark current images based on radiation detected by said radiation detection unit during a time from the instant said instruction unit issues the imaging start instruction to the instant radiation irradiation starts;
a second acquisition unit configured to acquire a radiation image based on radiation detected by said radiation detection unit;
a correction data generation unit configured to generate correction data corresponding to the radiation image acquired by said second acquisition unit, based on the plurality of dark current images acquired by said first acquisition unit; and
a correction unit configured to execute dark current correction processing for the radiation image acquired by said second acquisition unit, by using the correction data generated by said correction data generation unit.

11. A radiation imaging apparatus, for obtaining a radiation image of an object, the apparatus comprising:
an irradiation unit;
a radiation detection unit configured to detect radiation;
an instruction unit configured to issue a radiation imaging start instruction;
a setting unit configured to set an irradiation delay period between the time said instruction unit issues an imaging start instruction and the time irradiation by said irradiation unit starts;
a first acquisition unit configured to acquire a plurality of dark current images, from said radiation detection unit, during the irradiation delay period set by said setting unit;
a second acquisition unit configured to acquire a radiation image of the object from said radiation detection unit after the end of the irradiation delay period set by said setting unit;
a correction data generation unit configured to generate correction data, for the radiation image acquired by said second acquisition unit, based on the plurality of dark current images acquired by said first acquisition unit; and
a correction unit configured to execute dark current correction processing of the radiation image acquired by said second acquisition unit, by using the correction data generated by said correction data generation unit.

12. A radiation imaging method comprising:
detecting radiation transmitted through an object;
issuing a radiation imaging start instruction;
a dark-current image acquiring step of acquiring a plurality of dark current images based on radiation detected in said detecting step during a time from the instant at which the imaging start instruction is issued in said issuing step to the instant radiation irradiation starts;
a radiation-image acquiring step of acquiring a radiation image based on radiation detected in said detecting step;
generating correction data corresponding to the radiation image acquired in said radiation-image acquiring step, based on the plurality of dark current images acquired in said dark-current image acquiring step; and
executing dark-current correction processing for the radiation image acquired in said radiation-image acquiring step, by using the correction data generated in said generating step.

13. A non-transitory computer-readable storage medium storing, in executable form, a program for causing a radiation imaging apparatus to implement the method of claim 12.

14. A radiation imaging method, for obtaining a radiation image of an object, the method comprising:
issuing a radiation imaging start instruction;
setting an irradiation delay period between the time an imaging start instruction is issued in said issuing step and the time irradiation is actually started;
a dark-current image acquiring step, of acquiring a plurality of dark current images, from a radiation detection unit, during the irradiation delay period set in said setting step;
a radiation-image acquiring step, of irradiating the object and acquiring a radiation image of the object from the radiation detection unit after the end of the irradiation delay period set in said setting step;
generating correction data, for the radiation image acquired in said radiation-image acquiring step, based on the plurality of dark current images acquired in said dark-current image acquiring step; and
executing dark-current correction processing of the radiation image acquired in said radiation-image acquiring step, by using the correction data generated in said generating step.

15. A non-transitory computer-readable storage medium storing, in executable form, a program for causing a radiation imaging apparatus to implement the method of claim 14.

* * * * *